United States Patent [19]

Roninson

[11] Patent Number: 4,675,283

[45] Date of Patent: Jun. 23, 1987

[54] DETECTION AND ISOLATION OF HOMOLOGOUS, REPEATED AND AMPLIFIED NUCLEIC ACID SEQUENCES

[75] Inventor: Igor Roninson, Chicago, Ill.

[73] Assignee: Massachusetts Institute of Technology, Cambridge, Mass.

[21] Appl. No.: 632,512

[22] Filed: Jul. 19, 1984

[51] Int. Cl.[4] .................... C12Q 1/68

[52] U.S. Cl. .................... 435/6; 435/18; 435/91; 435/803; 436/501; 424/1.1; 204/182.8; 935/76; 935/77; 935/78

[58] Field of Search .................... 424/1.1; 436/501; 935/1, 2, 6, 9, 10, 11, 19, 76, 77, 78; 435/6, 91, 803, 18, 803; 204/182.8

[56] References Cited

U.S. PATENT DOCUMENTS

| | | | |
|---|---|---|---|
| 4,358,535 | 11/1982 | Falkow et al. | 424/2 |
| 4,395,486 | 7/1983 | Wilson et al. | 435/7 |
| 4,399,216 | 8/1983 | Axel et al. | 935/11 |
| 4,532,220 | 7/1985 | Lavi | 935/6 |

*Primary Examiner*—Christine M. Nucker
*Assistant Examiner*—Stephen C. Wieder
*Attorney, Agent, or Firm*—Paul J. Cook

[57] ABSTRACT

A novel method for detecting and isolating DNA sequences commonly held by different DNA preparations or repeated or amplified within a complex genome has been provided. The DNA preparations of interest are digested with the same restriction enzyme and a portion of at least one preparation is labeled with $^{32}P$. The labeled and unlabeled DNA preparations are combined and electrophoresed in an agarose gel. Following electrophoresis, the DNA is denatured in situ and allowed to reanneal within the gel so that homologous DNA sequences present within restriction fragments of the same size can reanneal. After reannealing, unhybridized single-stranded DNA is digested in situ followed by detection of the reannealed DNA by autoradiography. When labeled and unlabeled DNAs are derived from different DNA preparations, only the restriction fragments commonly held by these two preparations are detected. When a restriction digest of total eukaryotic DNA is reassociated in the gel by this procedure, repeated restriction fragments are selectively detected. This approach permits detection of selectively amplified DNA sequences and identification of the DNA sequences that have been commonly amplified in different cell populations. Localized of homologous, repeated or amplified DNA fragments of interest within the gel permits size-purification of such fragments.

11 Claims, 4 Drawing Figures

DETECTION AND ISOLATION OF HOMOLOGOUS, REPEATED AND AMPLIFIED NUCLEIC ACID SEQUENCES

The Government has rights in this invention pursuant to Grant Numbers NIH-5-R01-AM13945-13 and NIH-5-R01-CA33297-02 awarded by the Department of Health and Human Services.

FIELD OF THE INVENTION

The present invention is concerned generally with the characterization of individual nucleic acid sequences comprising the deoxyribonucleic acids or ribonucleic acids and is directly concerned with methods for the detection and isolation of homologous, repeated and amplified nucleic acid sequences in prokaryotic and eukaryotic genomes.

BACKGROUND OF THE INVENTION

Much of our present knowledge regarding the structure and function of deoxyribonucleic acid (hereinafter "DNA") has come from studying the genetic coding properties of DNA isolated from prokaryotic and eukaryotic genomes. It is known that the single chromosome of prokaryotes contains a single DNA molecule which is almost entirely a unique, a non-repeated sequence of a few hundred thousand to a few million base pairs in sequence. The chromosomes of eukaryotes, being much more complex, generally contain much more DNA per genome than is needed to code for all the proteins required for cell function. Eukaryotic DNA sequences have thus been divided into three categories based on the degree of their reiteration in the genome: single copy DNA, which includes the coding sequences for the main proteins of the cell; these single copy DNA sequences characteristically comprise 40–80% of the total DNA in the cell. Moderately repeated DNA includes those DNA sequences that are repeated from 2 to $10^5$ times within the genome; some of these sequences code for major macromolecules of the cell including ribosomal and transfer RNAs and such proteins as histones, globins or immunoglobulins, while other sequences may play a regulatory or structural role in the genome. Highly repeated DNA represents those DNA sequences which have been repeated in greater than $10^5$ copies; the function of these sequences is not clearly understood at the present time. Both moderately and highly repeated DNA sequences can be arranged in either of the two different modes. In the first type of arrangement, the basic structural units of a repeated sequence are interspersed at different locations in the genome and linked to single copy sequences. In the second type of arrangement, the basic structural units are linked to each other in long tandem arrays. When total genomic DNA is digested with a restriction enzyme, that disrupts DNA at specific sites, the *interspersed* repeated sequences give rise to a series of identical restriction fragments only if the basic structural unit of such sequences contains two or more sites that are recognized by the restriction enzyme; if less than two restriction sites are present within the structural unit, the restriction enzyme digestion gives rise to a heterogeneous mixture of fragments containing different single copy DNA sequences linked to the same repeated sequence. On the other hand, the presence of only one restriction site in the basic structural unit of a *tandemly* repeated sequence is sufficient to convert such a sequence into a series of identical restriction fragments. This differential response to restriction enzyme digestion is important in the determination of the type of arrangement of a repeated DNA sequence in the genome.

Much of our present knowledge regarding individual DNA sequences comes from experiments in which genomic DNA is digested using restriction endonucleases followed by agarose gel electrophoretic separation of the DNA fragments. The individual bands containing DNA fragments of various molecular weight have been immobilized by transfer onto nitrocellulose filters [Southern, *J. Mol. Biol.* 98:503–517 (1975)] or in dried agarose gels [Shinnick et al., *Nuc. Acids Res.* 2:1911–1929 (1975)] and the restriction fragments subsequently hybridized by a combination with exogenously added DNA or RNA probes containing a radioactive label. After washing out the nonhybridized radioactive material, the locations of the hybrids are determined by autoradiography. These techniques, however, require that the DNA or RNA sequences in the probe be complementary to the DNA in the restriction fragments only at a limited number of sites so that an interpretable pattern can be obtained upon autoradiography. There is no requirement (and often no desire) for complete homology in the probe for the DNA sequences in the restriction fragments.

The ability of the probe to hybridize with less than completely homologous DNA fragments often creates a severe problem when the probe comprises a genomic clone of eukaryotic DNA for hybridization with a restriction digest of total genomic DNA. Under these conditions, the frequent presence within the cloned probe of short interspersed repeated DNA sequences results in a smeared autoradiography pattern due to hybridization of the repeated sequences within the probe with a great number of different restriction fragments containing the same repeated sequence linked to different single copy sequences [Fisher et al., *Proc. Natl. Acad. Sci. USA* 81:520–524 (1984)]. The data obtained under such test conditions is often confusing and frequently undecipherable.

The deficiencies of presently known methods of analyses and detection become even more apparent in view of recent studies which demonstrated that selective amplification of specific DNA sequences is a common mechanism for adaptation of eukaryotic cells to a variety of selective conditions including drug resistance [Stark and Wahl, *Ann. Rev. Biochem.* 53:447–495 (1984)]. Amplification of individual genes was also found to occur in some developmental processes and has been suggested as a mechanism in carcinogenesis and tumor progression [Cowell, *Ann. Rev. Genet.* 16:21–59 (1982); Pall, *Proc. Natl. Acad. Sci. USA* 78:2465–2468 (1981); Varshavsky, *Cell* 25:561–572 (1981)]. The existing DNA hybridization techniques provide for the detection of amplified genes only if such genes have already been cloned and are available for use as probes. On the other hand, amplification of certain uncloned genes can provide a unique opportunity for their isolation, given the possibility of identification of amplified DNA sequences within the genome solely on the basis of their amplification. Amplified DNA sequences are defined as those sequences that have become reiterated relatively recently, e.g. in the course of selection for drug resistance or in the course of carcinogenesis, as opposed to the repeated DNA sequences that are always found in multiple copies in the genome of a given organism. The existing approaches towards this goal have included the purification of chromosomal structures known to contain amplified DNA [George and Powers, *Cell* 24:117–123 (1981); Kanda et al., *Proc. Natl. Acad. Sci. USA* 80:4069–4073 (1983)] and the cloning of amplified DNA sequences after differential screening with genomic probes [Brison et al., *Mol. Cell, Biol.* 2:578–587 (1982)]. None of these techniques provide for the rapid detection of amplified genes in cellular DNA preparations or comparison of amplified individual DNA sequences between different DNA preparations prior to cloning such amplified DNA sequences and their subsequent use as probes. A more general approach involves detection of highly amplified restriction fragments of DNA as bands that become detectable upon ethidium bromide staining of the gel [Heintz & Hamlin, *Proc. Natl. Acad. Sci. USA* 79:4083–4087 (1982); Tyler-Smith & Bostock, *J. Mol. Biol.* 153:203–218 (1982)]. The sensitivity of this method, however, is very low in that the DNA sequences within the restriction fragments must be repeated at least several hundred times per mammalian genome before they can be detected as distinct bands against the background produced by heterogeneous single copy DNA fragments.

It is apparent, therefore, that there is a substantial need for a general method for the detection and characterization of amplified individual nucleic acid sequences, especially for the analysis of those systems where the nature of the amplified genes is presently unknown and/or there are no cloned probes yet available. The need for a sensitive and precise assay method is most critical when the selectively amplified DNA sequences have been amplified from two to two hundred times, as is the situation in most cases of gene amplification.

SUMMARY OF THE INVENTION

A novel method for detecting DNA segments that are shared by different DNA preparations, as well as repeated and amplified DNA segments within a DNA preparation of interest is provided comprising the steps of:

(1) Reacting the DNA preparations of interest with the same restriction enzyme or combination of several restriction enzymes to yield reaction products comprising a plurality of DNA fragments;

(2) Introducing a radioactive or some other identifiable label into portions of the reaction products in such a way that the electrophoretic mobility of the labeled DNA fragments remains unchanged;

(3) Combining a labeled DNA product with an excess of an unlabeled reaction product derived either from the same or from a different DNA preparation and subjecting the mixture to gel electrophoresis;

(4) Denaturing in situ the DNA fragments in said electrophoresed mixture to yield single-stranded DNA fragments;

(5) Renaturing said single-stranded DNA fragments to convert a portion of them into hybridized double-stranded fragments;

(6) Disrupting the single-stranded DNA sequences in situ; and (7) Identifying the labeled DNA sequences within the hybridized double-stranded fragments, either immediately or after repeating steps (4)–(6) one or more times.

When two different DNA preparations are hybridized with each other using this methodology, DNA fragments of identical electrophoretic mobility and having homologous sequences can be detected. When a restriction enzymatic digest of a total eukaryotic DNA preparation is reassociated in situ using the above procedure, individual repeated DNA sequences can be detected and visualized by autoradiography. The intensity of the bands in an autoradiogram correlates with the degree of reiteration of the corresponding fragments in the genome. Amplified DNA fragments can be identified by comparison of the repeated fragments detectable in a DNA preparation of interest and in a control DNA preparation. Once the position of an individual DNA fragment of interest has been located in the gel by the above methodology, such a fragment can be purified and cloned by the procedure comprising the steps of:

(8) Purifying the DNA fragment of interest by excising a narrow strip of the gel containing said fragment and isolating DNA from the gel either immediately, or after further purification steps that are feasible for repeated or amplified DNA fragments, as described below;

(9) Denaturing in situ the DNA fragments in the gel strip and renaturing said fragments to convert DNA into a mixture of single-stranded and double-stranded fragments, wherein the latter moiety is selectively enriched for the fragment of interest;

(10) Isolating said mixture from the gel strip and selectively joining double-stranded DNA fragments to a cloning vector;

(11) Introducing the resulting recombinant DNA molecules into bacteria and cloning them by standard techniques; and

(12) Testing individual clones for the presence of amplified or repeated DNA fragments by using them as probes for hybridization with genomic DNA preparations or by any other convenient screening procedure.

DETAILED DESCRIPTION OF THE DRAWINGS

The detailed description of the present invention may be more clearly and fully understood when taken in conjunction with the accompanying drawing, in which.

DETAILED DESCRIPTION OF THE PREFERRED EMBODIMENT

Figure 1:
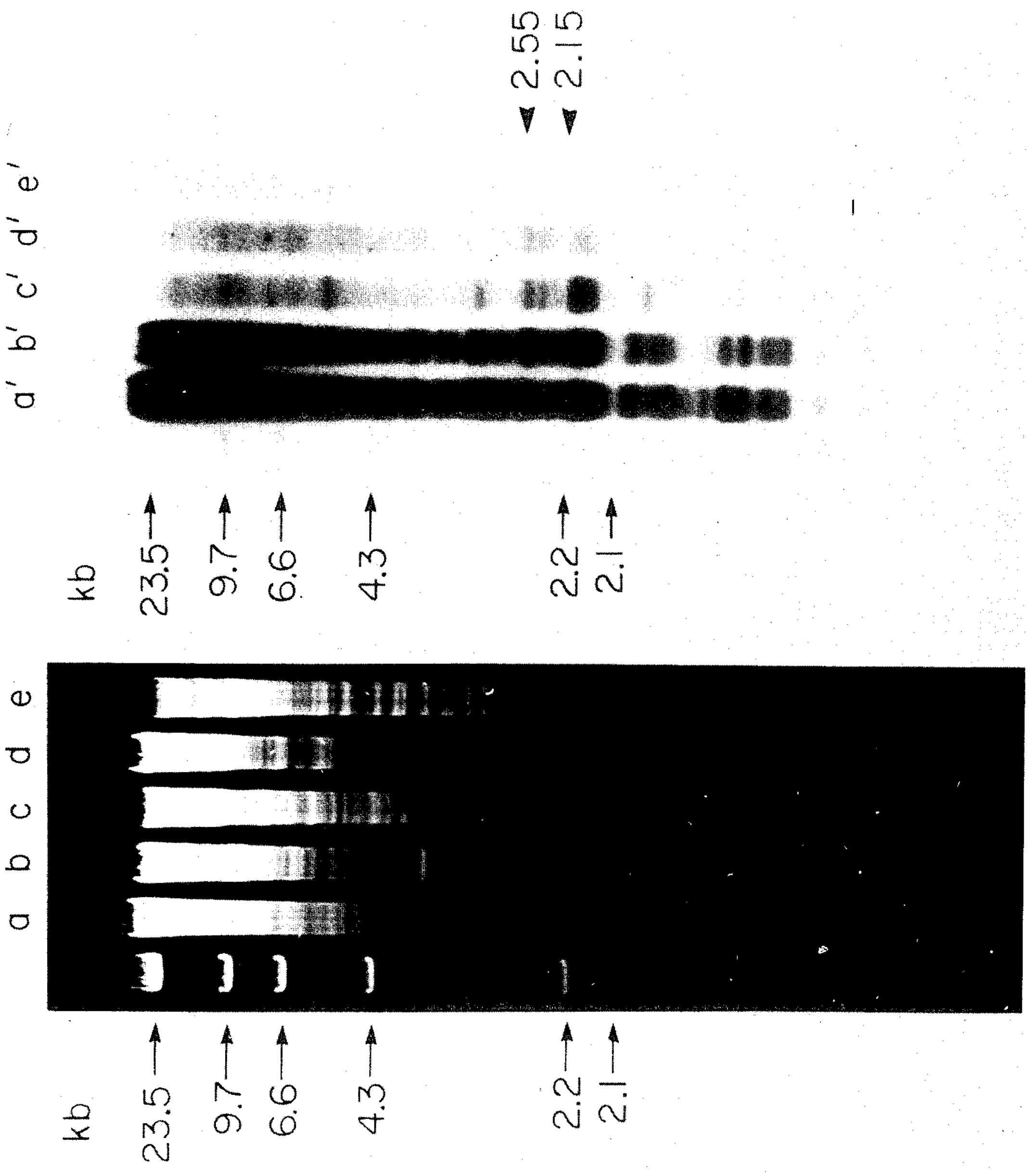
FIG. 1 is an autoradiogram identifying commonly held EcoRI restriction fragments in bacterial genomes.

The present invention is a novel method of DNA hybridization that combines the advantages of electrophoretically separated restriction digest DNA fragments with the ability to utilize complex eukaryotic and/or prokaryotic genomes as hybridization probes. Restriction enzyme generated fragments containing a radioactive or otherwise identifiable label (hereinafter "tracer") are combined with an excess of unlabeled DNA digested with the same restriction enzyme (hereinafter "driver"), are coelectrophoresed in a gel such as agarose, and are hybridized in situ. Hybridization can thus occur only between DNA fragments of the same size; consequently, hybridization of different kinds of DNA using this procedure (hereinafter "in-gel renaturation" or "in-gel hybridization") permits identification of restriction fragments held in common by these genomes. When a restriction digest of total eukaryotic DNA is subjected to in-gel renaturization, repeated individual DNA sequences present in sufficient concentration to effectively reanneal within the gel can be detected.

Two factors are crucial for the successful renaturation of individual DNA sequences in gel matrices:

(1) The labeled (tracer) DNA fragments should be undegraded so that their electrophoretic mobility would be the same as for the unlabeled (driver) DNA fragments; and (2) The unhybridized single-stranded DNA which is formed as a concommitant byproduct during reannealing should be completely removed from the gel.

The first requirement is fulfilled by using the replacement synthesis procedure for labeling of the tracer DNA [Challberg & Englund, *Method Enzymol.* 65:39–42 (1980)]. This technique employs exonucleolytic degradation of DNA using the 3'→5' exonuclease activity of T4 DNA polymerase followed by efficient resynthesis of degraded ends to obtain intact DNA fragments of high specific activity. An additional advantage of using this procedure is that distribution of label (preferably $^{32}$P radionuclide) in the tracer can be controlled by varying the extent of the exonuclease reaction. In many instances it is preferred to limit the radioactive label to the terminal portions of the restriction fragments.

The second crucial condition is fulfilled by optimizing the conditions for in situ digestion of DNA using the single-strand specific nuclease S1. It was found that incubation of restriction enzyme digested DNA with 50–100 units per milliliter (hereinafter "ml") of S1 nuclease for two hours followed by elution of the digested material from the gel results in complete removal of single-stranded DNA. Detailed use conditions for degradation of denature DNA following gel renaturation are described below.

It will be appreciated by those ordinarily skilled in this art that this methodology is suitable for analysis of any double-stranded nucleic acids, including DNA-RNA hybrids and double-stranded RNA molecules and that the specific optimum concentrations and conditions described herein may be varied at will to meet the user's convenience or specific needs. It will be recognized that many of the basic techniques employed as part of the present invention are not novel in and of themselves but have become established techniques of molecular cloning in the art. Such techniques are well described in Maniatis et al., *Molecular Cloning, A Laboratory Manual*, Cold Spring Harbor Laboratory, 1982 and in Davis et al., *Advanced Bacterial Genetic Engineering*, Cold Spring Harbor Laboratory, 1980.

For the purposes of clarity and a fuller understanding of the methodology comprising the present invention, a detailed description of the materials and each of the manipulative steps comprising the present process will be given:

Materials

Restriction endonucleases, the large fragment of DNA polymerase I, T4 DNA polymerase, S1 nuclease,-[α-$^{32}$P] dCTP (3,000 Ci/mM in 50% ethanol), agarose and formamide were all obtained from commercial sources.

Plasmid DNA was prepared according to Kretschmer et al. [*J. Biol. Chem.* 255:3204–3211 (1980)]. Lambda phage DNA was commercially obtained. Eukaryotic DNA preparations were made by the procedure of Blin and Stafford [*Nucl. Acids Res.* 3:2303–2309 (1976)]. DNA concentration was determined by diphenylamine assay [Giles & Myers, *Nature* 206:93 (1965)]. The number of the dihydrofolate reductase (hereinafter "DHFR") gene copies in DNA from MTX-resistant cells was determined by dot blot hybridization [Kafatos et al., *Nuc. Acids Res.* 7:1541–1552 (1979) and Snapka & Varshavsky, *Proc. Natl. Acad. Sci. USA* 80:7533–7537 (1983)].

Single-stranded end-labeled fragments of plasmids pCGρ1 and pCGε1 were prepared by digesting the plasmids with Hind II and Msp I followed by 3' end-labeling using the large fragment of DNA polymerase I and α-$^{32}$P-dTTP as described in Roninson & Ingram [*Proc. Natl. Acad. Sci. USA* 78:4782–4785 (1981)]. The labeled fragments were purified from agarose gels as described in Roninson & Ingram [*Cell* 28:515–521 (1982)] and strand-separation was performed according to the procedure of Maxam and Gilbert [*Meth. Enzymol.* 65:499–560 (1980)].

Labeling of Tracer DNA

To ensure complete restriction enzyme digestion, five units of enzyme per 1.0 microgram (hereinafter "μg") of DNA were used. Tracer DNA labeled by replacement synthesis with T4 DNA polymerase and [α-hu 32P] dCTP following the method of O'Farrell, *Focus* 3:1–3 (1981). Other procedures for radioactive labeling that do not result in degradation of DNA fragments can also be used at convenience. Such procedures include, for example, replacement synthesis by consecutive use of exonuclease III and the large fragment of DNA polymerase I, nick-translation by DNA polymerase I under conditions of limited deoxyribonuclease activity, and in vivo labeling of DNA prior to extraction and restriction enzyme digestion. It is preferred that radionuclides such as phosphorus or sulfur isotopes be used as the label of choice; however, any other identifying non-radioactive label, such as a chemical modification that permits subsequent enzymatic or immunochemical detection of amplified DNA, may be substituted and used as desired, providing that the electrophoretic mobility of tracer DNA is unaltered by the modification. It is also understood that when tracer and driver DNA are derived from the same DNA preparation, the step of tracer labeling may be omitted, and DNA sequences may be identified after in-gel renaturation by staining or another similar procedure.

In the exonuclease reaction, 0.2–1.0 μg of DNA were combined with two units of T4 DNA polymerase in 10.0 microliters (hereinafter "μl") of reaction buffer at 37° C. The composition of the reaction buffer is 33 mM Tris-acetate pH 7.9/65 mM Na acetate/10.0 mM Mg acetate/100 μg/ml bovine serum albumin/0.5 mM dithiotreitol. The time of the exonuclease reaction varied from 15–60 minutes for labeling phage or plasmid DNA and 3–5 minutes for labeling total eukaryotic DNA.

For resynthesis of the degraded strands, this mixture was transferred into a tube containing 70–150 μCi of dry [α-$^{32}$P] dCTP and 80 μM each of dATP, dGTP and dTTP, each added in a final volume of 25 μl of the reaction buffer. After incubation at 37° C. for 30 minutes, 80 μM of unlabeled dCTP was added and the reaction allowed to continue for 20 minutes more in order to ensure complete regeneration of the duplexes. The reaction was stopped subsequently by the addition of four volumes of 2.5M ammonium acetate and 10 $\mu g$ tRNA and the DNA was precipitated with three volumes of ethanol. The precipitate was redissolved in 100 $\mu l$ of 2.5 M ammonium acetate followed by precipitation of the DNA with ethanol a second time. This second precipitate was rinsed with 70% ethanol and dissolved in a convenient volume of 10 mM Tris-HCl, pH 7.5/1 mM EDTA.

Gel Electrophoresis

Electrophoresis is preferably performed using agarose gels in the conventionally known manner but may also be employed using polyacrylamide and other gel matrices. The amount of labeled tracer DNA used for electrophoresis varied from 500 disintegrations per minute (hereinafter "dpm") in phage DNA digests to $5-15\times10^6$ dpm for eukaryotic DNA digests. The tracer DNA was mixed with varying amounts of unlabeled driver DNA ranging from 50 picogram (hereinafter "pg") to 15 microgram (hereinafter "$\mu g$".

In all instances, the mixtures comprising unlabeled driver DNA and labeled tracer DNA were loaded onto horizontal gel slabs of 1% agarose in Tris-acetate buffer comprising 22.5 mM Tris-acetate, pH 8.3/10 mM Na acetate/1 mM EDTA. The dimensions of the gel slab were $30.5\times24\times0.4$ cm with the sample wells being 9 mm wide and 2 mm thick. Gel slabs and sample wells of any other sizes can be used at convenience. The sample volume was 25-30 ul. Electrophoresis was performed in Tris-acetate buffer containing 0.5 ml/l ethidium bromide at 50 volts in the conventionally known manner. Other electrophoretic conditions can be used at convenience. Following electrophoresis, the gels were photographed using a 360 nm wavelength ultraviolet illuminator to confirm the appropriate separation of DNA fragments. Other methods for effecting separation of DNA molecules other than gel electrophoresis that can be utilized in this process include, for example, chromatography in a solid or semi-solid support.

In-Gel Renaturation

After electrophoresis, each gel slab was cut into a $28.5\times16.3$ cm size and carefully transferred into a $29.0\times16.5\times5.0$ cm flat bottom polypropylene box. Other types of plastic or glass containers can be used if desired. For boxes of a different size, the volumes of all solutions should be appropriately adjusted. All of the subsequent manipulative steps were performed with constant shaking on a rotary table at a speed varying from 20-80 rpm. Each of the solutions used in denaturation or reannealing were warmed to the appropriate temperature prior to use.

The DNA fragments in the electrophoresed reaction product were denatured by soaking the gel in 350 ml of the denaturing buffer containing 0.5M NaOH/0.6M NaCl and 0.004% thymol blue at 37° C. After 30 minutes incubation, an identical volume of fresh denaturing buffer was added and the process allowed to continue for an additional 30 minutes. It is believed that substitution of alkali for other DNA denaturing agents, whether chemical or thermal, would constitute mere variations of the preferred procedure. It is also understood that DNA can be denatured prior to electrophoresis, and electrophoresis can be conducted under alkaline conditions. This modification of the preferred procedure would not require denaturation of DNA subsequent to electrophoresis.

The gel was then neutralized by washing the matrix with 350 ml volumes of hybridization buffer containing 50% formamide/50 mM Na phosphate, pH 7.0/0.9 M NaCl/0.5 mM EDTA at 45° C. It is preferred that the gel be washed 4 to 5 times with the hybridization buffer for 15-20 minutes at each washing. Neutralization of the gel is initially indicated by the appearance of a yellow color from the thymol blue in the gel after which the pH of the washing buffer is monitored using pH indicator sticks.

Renaturing the DNA then occured by incubating the gel in 350 ml of the hybridization buffer for a period of from 2 to 20 hours at 45° C. Renaturation can also be performed in buffers with a different content of formamide and different salt concentrations, at temperatures ranging from 37° C. to 68° C., depending on the composition of the renaturation buffer.

The optimum conditions for DNA renaturation-hybridization in agarose gels were identified.

It was found that the protection of tracer DNA from subsequent digestion with S1 nuclease varied with the amount of driver DNA present in the gel. The minimal amount of driver DNA necessary for detection of the tracer under the described conditions of hybridization was approximately 5 pg per band as determined for DNA restriction fragments of 2 kilobase (hereinafter "kb") size. This level of sensitivity was achieved after 2 hours of hybridization following neutralization of the gel. Hybridization for longer periods of time (up to 20 hours duration) resulted in only a slight increase in the intensity of DNA bands. Similarly, hybridization under conditions of twofold higher ionic strength allowed one to detect as little as 2.5 pg of DNA per band. While there was some variation in the intensity of different bands due to inefficient labeling of some tracer DNA fragments and a consistently observed lower sensitivity for DNA fragments larger than 15 kb, the efficiency of renaturation for most fragments was relatively constant at a given molar concentration.

Disruption In Situ of Single-Stranded DNA

After hybridization, the gel was washed with 350 ml of S1 nuclease digestion buffer 5 times for 20 minutes duration each time. The digestion buffer contained 50 mM Na acetate, pH 4.6/0.2 M NaCl/ and 1 mM $ZnSO_4$. S1 nuclease digestion was performed using 50-100 units/ml of S1 nuclease in 250 ml of the digestion buffer and allowing the reaction to continue for 2 hours.

The optimum conditions for in situ digestion of DNA using S1 nuclease were determined by combining double-stranded and single-stranded DNA fragments from recombinant plasmids pCG$\rho$1 and pCG$\epsilon$1 and coelectrophoresing them in a 1.5% agarose gel. Duplicate gels were washed with the S1 nuclease digestion buffer and incubated with varying amounts of S1 nuclease ranging from 5 to 150 units/ml at 37° C. It was found that incubation with 50 units/ml of S1 nuclease for 2 hours followed by elution of the digested material from the gel resulted in complete removal of all single-stranded DNA with only limited degradation of double-stranded fragments. Although both the concentration of S1 nuclease and the duration and temperature of reaction may be varied, it is believed that all variances from the optimum conditions described herein are merely variations of personal choice or convenience. It is also appreciated that other single-strand specific nuclease such as, for example, mung bean nuclease can be used for in situ disruption of single-stranded DNA molecules. Other means of selection for double-stranded DNA, such as selective transfer of it, onto a solid support are also believed to be mere variations of the described procedure.

Following S1 nuclease treatment, the digestion products were eluted from the gel by washing with 300–400 ml volumes of 30 mM Na phosphate, pH 7.0/0.54 M NaCl/3 mM EDTA/0.1% sodium dodecylsulphate for a total of 2 to 3 hours. The composition of the elution buffer is not essential and it can be varied at convenience. It is preferred that 3 changes of buffer be made during the 2 hours washing time. After elution, the gel is dried in a gel slab dryer (commercially available) and autoradiographed using Kodak XAR-5 or a similar X-ray film either with or without an intensifying screen. In many instances, it is desirable that immediately following the S1 nuclease digestion, the gel is placed in denaturing buffer again, and the entire hybridization procedure and S1 nuclease treatment repeated in sequence once more prior to autoradiography.

Cloning Amplified DNA Fragments

Mammalian DNA (100–200 μg) was digested with a restriction enzyme and electrophoresed in an agarose gel, 15 μg of unlabeled DNA having been loaded onto each lane. Position of the amplified fragment of interest was established by in-gel renaturation of the lanes containing the same DNA restriction digest, a portion of which had been labeled with $^{32}P$ ($10^7$ dpm in 15 μg of DNA) and electrophoresed in the same gel. A narrow strip of the gel containing the fragment of interest was excised and subjected to 2 cycles of in situ denaturation and renaturation as described above. S1 nuclease was not used in this protocol so that the reannealed fragments would retain the cohesive ends generated by the restriction enzyme. The mixture of single-stranded and double-stranded DNA (the latter moiety enriched in amplified DNA fragments afer renaturation) was eluted from the gel by a conventional procedure. It is believed that the use of only one or more than two cycles of denaturation and renaturation or the addition of single-strand specific nuclease digestion steps to the above protocol would be mere variations of this procedure. Said mixture was ligated to a plasmid vector that had been cleaved with the same restriction enzyme. Only double-stranded DNA could be ligated at this step. Other types of cloning vectors can also be used depending on the personal preference. The recombinant plasmids were used to transform *Escherichia coli* by a conventional procedure to yield bacterial colonies containing individual recombinant DNA clones. In order to identify the clones containing the amplified fragment of interest, DNA from individual colonies was isolated by the procedure of Dagert & Ehrlich [*Gene* 6:23–28 (1979)] and analyzed by digestion with restriction enzymes and agarose gel electrophoresis. Production of identical restriction patterns by a number of plasmids indicated that the corresponding clones contained DNA inserts that were reiterated in the genome. DNA from one of these clones was used as a probe for hybridization with a restriction digest of genomic DNA by the procedure of Southern [*J. Mol. Biol.* 98:503–517 (1975)] to confirm amplification of the cloned DNA sequence in the genome. It is appreciated that, depending on personal choice and convenience, other protocols can be used for selecting the clones containing amplified or repeated DNA sequences from the plurality of clones obtained by the above procedure. These include, for example, testing individual clones for amplification in the genome by using them as tracers with genomic DNA being used as the driver in the ingel renaturation procedure. Transcribed DNA clones can also be selected by colony hybridization with a radioactively labeled DNA probe complementary to messenger RNA from the cells where the cloned sequence is transcribed; whereas, recombinant DNA with homology to any cloned DNA sequence of interest can be identified by using such sequence as a probe.

The methodology comprising the present invention and the range of applications for which it may be used is demonstrated by the Examples which follow. It will be expressly understood, however, that these Examples are merely illustrative of the various fields of use to which this invention may be applied and that the Examples in no sense restrict or limit the present invention in either form or scope.

EXAMPLE I

Identification of homologous fragments having the same size.

This technique may be used to identify common restriction fragments (within the limits of resolution of agarose gel electrophoresis) between the DNA of *E. coli* and four other species of bacteria, namely, *Shigella flexneri, Salmonella typhimurium, Proteus mirabilis* and *Staphylococcus aureus*. The genomes of these latter bacteria are recognized as having a different degree of overall sequence homology to the genome of *E. coli* [Brenner et al., *J. Bacteriol.* 98:637–650 (1969)]. The DNA of *E. coli* strain AB 1157 (which does not contain any detectable plasmid DNA) was digested with EcoRI and labeled to a specific activity of $7.6\times10^7$ dpm/μg when an average of 750 nucleotides were excised from each 3′ end in the exonuclease reaction. 4 ng (corresponding to $3\times10^5$ dpm) of *E. coli* tracer DNA were mixed with 2.5 μg of EcoRI digest of each bacterial DNA under test. The results are illustrated in FIG. 1 in which lane a/a′ contains *E. coli* DNA as a driver; lane b/b′ contains DNA from *S. flexneri*; lane c/c′ is DNA from *S. typhimurium*; lane d/d′ represents DNA from *P. mirabilis* and lane e/e′ is *S. aureus*. Lanes a–e represent ethidium bromide staining patterns of the gel prior to hybridization, while lanes a′–e′ represent autoradiograms of the dry gel after one cycle of in-gel hybridization. Hybridization was performed in 30 mM Na phosphate, pH 7.0/0.54 M NaCl/3 mM EDTA/50% formamide for 2 hours at 37° C. followed by digestion with 100 units/ml S1 nuclease. Autoradiography was done overnight.

The autoradiogram indicates a correlation with the known degrees of sequence homology determined by other techniques. For example, the Shigella DNA is noted to have an 86% sequence homology with *E. Coli* and the number of common EcoRI fragments in lane b′ between these genomes is clearly too high to be counted; the degree of hybridization, however, is clearly below that observed in lane a′ where *E. coli* DNA alone was tested. Salmonella DNA is known to have 38% homology to *E. coli* and lane c′ shows only 10 common EcoRI fragments ranging in size from 5.2 to 0.75 kb to be detectable. The DNA of *P. proteus* is only 5% homologous to *E. coli* DNA and lane d′ contains four EcoRI fragments that hybridize with *E. coli* DNA fragments of the same size, although the weak appearance of the corresponding bands suggests that homology is less than complete. DNA of *S. aureus* in lane e' does not reveal any EcoRI fragments in common with *E. coli*, as expected. The presence of labeled material at the top of lanes c', d' and e' is believed due to residual reassociation of *E. coli* tracer DNA which was significantly decreased when lower quantities of tracer DNA were used. Novel information is also presented by the appearance of two EcoRI fragments of a 2.55 and 2.15 kb size (indicated by arrows) which appeared to be shared in common by the DNAs of all four *Enterobacteriaceae.* The existence of this highly conserved DNA sequence has not been revealed previously by methodologies now known. The nature and characterization of these highly conserved sequences remains yet to be revealed.

The present invention provides for identification of extended regions of homology not only between different genomes, as illustrated in the above Example, but also between isolated chromosomes, extrachromosomal DNA and mixtures of viral and bacterial DNA. Of particular importance is the application of this technique for detection of alterations in the structure or copy number of an individual cloned DNA sequence by hybridization between a recombinant DNA clone and genomic DNA. In this application, the clone can be used as a tracer and genomic DNA as a driver, or vice versa. In this method of hybridization, as opposed to the conventional techniques, the presence of interspersed repeated sequences in the cloned DNA should not affect the specificity of hybridization. This application will be particularly useful in the field of clinical diagnostics of genetic diseases, where it will greatly increase the choice of recombinant DNA clones for use as diagnostic markers.

EXAMPLE II

Repeated restriction fragments in human DNA.

The detection of individual DNA sequences repeated seriatim within a mammalian genome is demonstrated by the analysis of repeated fragments revealed by digestion of human DNA with HindIII restriction enzyme. DNA samples were extracted from peripheral blood lymphocytes of eight different leukemia patients. DNA was digested with HindIII as previously described. 1 μg of each DNA preparation was labeled with $^{32}P$ as described above, and $10^7$ dpm of the labeled tracer DNA were mixed with 15 μg of the same unlabeled DNA used as a driver. It should be noted that when tracer and driver DNA represent different parts of the same DNA preparation, as in this Example, the specific activity of tracer DNA and the ratio at which tracer and driver are mixed is of no importance and is determined by convenience. For the optimum detection of moderately repeated fragments, it is important, however, that the total amount of DNA loaded onto each lane be as large as possible without causing a distortion of the electrophoretic pattern. Under the preferred conditions, the maximum amount constitutes between 15 and 20 μg per lane.

Figure 2:
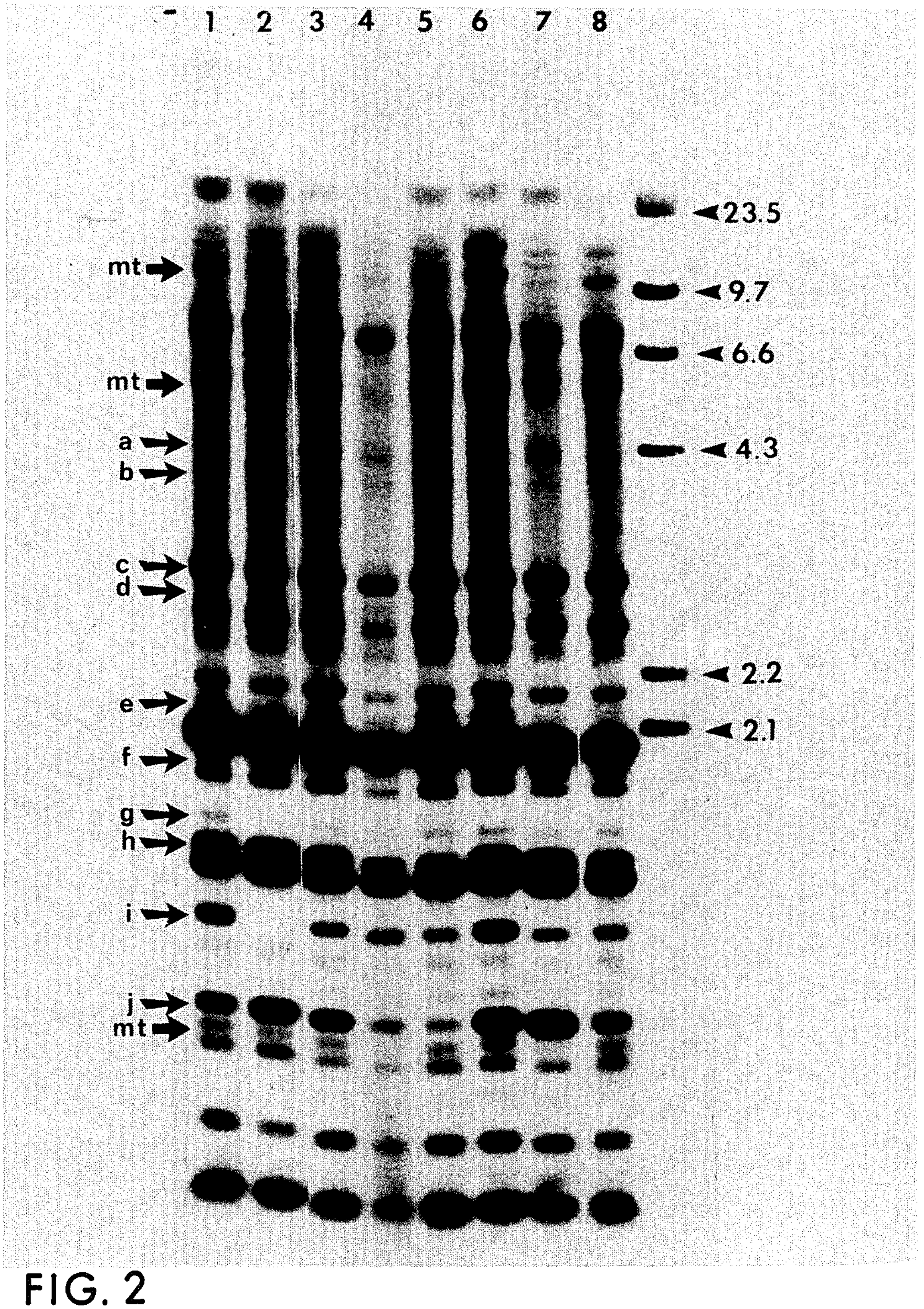
FIG. 2 is an autoradiogram illustrating the detection of repeated HindIII fragments in different human DNA preparations.

The mixtures were electrophoresed in a 1% agarose gel. After electrophoresis, the gel was subjected to two cycles of denaturation, renaturation and S1 nuclease in situ digestion, as described. The time of renaturation after neutralizing the gel was 2 hours during the first cycle and 10 hours during the second cycle. Autoradiography was performed overnight. The results are illustrated in FIG. 2 in which lanes 1–8 each represents a HindIII digest of DNA from individual patient. The HindIII fragments of λ phage DNA were used as standards for size determination.

As a result of in-gel renaturation, a number of bands corresponding to repeated fragments produced upon digestion of human DNA with HindIII are observed. Most of these fragments were undetectable by ethidium bromide staining or autoradiography prior to in-gel renaturation. Up to 30 bands of various intensity can be detected in each lane. 3 of these bands are known to correspond to HindIII fragments of human mitochondrial DNA (mt, indicated with arrows). The majority of other bands have not been detected in previous studies investigating repeated sequences in human DNA. It is of particular interest that the intensity of some of these bands varies significantly among different lanes. Fragments displaying a particularly high degree of polymorphism (a–j) are indicated with arrows in FIG. 2. As discussed previously, the repeated fragments observed upon digestion of genomic DNA with a restriction enzyme can be derived from the repeated sequences having either interspersed or tandem mode of arrangement. The former are more likely to produce repeated fragments than the latter, since the minimum number of restriction sites per basic structural unit required for generation of such fragments is just one for tandem repeats, but two for interspersed repeats. If at least some of the observed bands are derived from tandemly repeated sequences with a specific location in the genome, such bands can be used as markers for diagnosis of genetic diseases. Specifically, the bands whose copy number and therefore intensity are relatively constant, can be used for diagnosis of copy number alterations for the chromosomes from which these bands are derived, such as, for example, trisomy for chromosome #21, which results in Down's Syndrome. On the other hand, the variable bands can be used as polymorphic markers which can be linked to the genes for various human genetic diseases. The use of 40–50 different restriction enzymes should allow to develop a set of several hundred polymorphic markers spanning the entire human genome. The use of such set will permit quick identification of a marker that is linked to any given genetic disease and can be efficiently used for diagnosis.

EXAMPLE III

Amplified DNA sequences in methotrexate-resistant mouse cells.

It has been previously demonstrated that resistance to methotrexate (hereinafter "MTX") in mouse cell lines results from amplification of the gene coding for dihydrofolate reductase (hereinafter "DHFR"), the target enzyme for MTX [Alt et al., *J. Biol. Chem.* 253:1357-1370 (1978)]. Investigations have shown that various amounts of flanking DNA sequences preceding and following the gene itself are co-amplified with DHFR gene in different cell lines [Tyler-Smith & Bostock, *J. Mol. Biol.* 153: 203–218 (1981)]. Under such circumstances, it is possible to identify a subset of amplified DNA sequences that are commonly amplified in different independently derived MTX-resistant cell lines. Such a subset is likely to contain the DHFR gene together with only a small amount of flanking sequences.

In this Example, DNA from various mouse cell lines was digested with Bam HI endonuclease and subsequently $^{32}P$-labeled as previously described herein. The labeled tracer DNA was mixed with 10–12 μg of either identical or different unlabeled driver DNA, electrophoresed in 1% agarose gel, and subjected to two cycles of in-gel renaturation and S1 nuclease digestion under the same conditions as in Example II. Autoradiography was performed overnight. The results are illustrated in FIG. 3.

Figure 3:
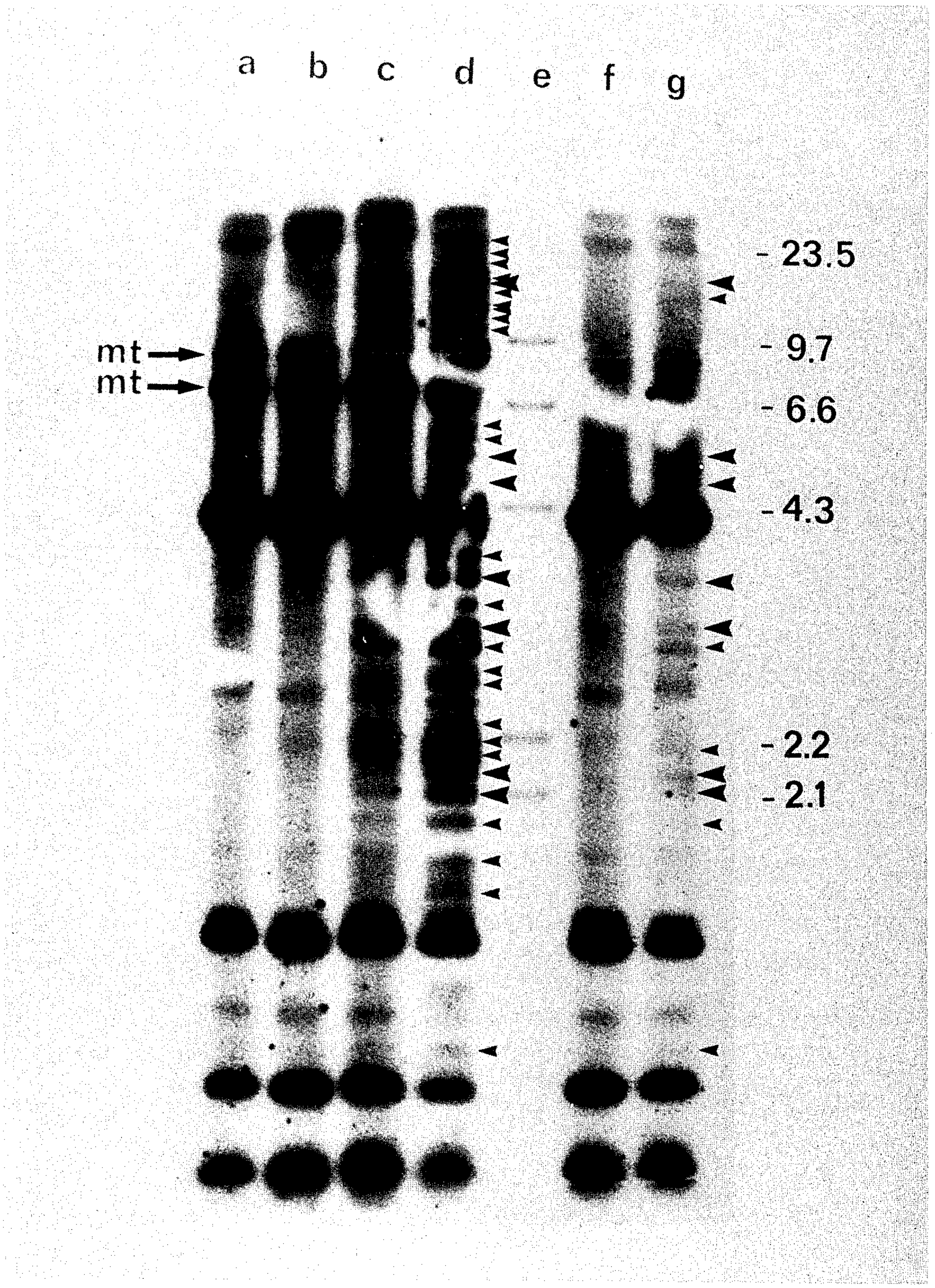
FIG. 3 is an autoradiogram illustrating the detection of amplified restriction fragments in methotrexate resistant mouse cell lines.

The autoradiogram represented in FIG. 3 contained the following:

In lanes a–f, identical DNAs were used both as tracer DNA and as unlabeled driver DNA. Lane a contains DNA from MTX-sensitive NIH 3T3 cells (one copy of the DHFR gene per haploid genome). Lane d contains only DNA from MTX-resistant R500 cells (170 copies of the DHFR gene). Lanes b and c contain mixtures of 3T3 and R500 DNA corresponding to either 20 copies in lane b or 50 copies in labe c of the DHFR gene per haploid genome. Lane f contains DNA from an independently derived MTX-resistant line, R.3 (16 copies of the DHFR gene). Lane g contains R.3 DNA as a tracer and R500 DNA as a driver.

The amount of tracer DNA was 1.0 μg in lanes a–d and 0.5 μg in lanes f and g. The amount of radioactivity in the tracer was $10^7$ dpm in lanes a and b, $9\times10^6$ dpm in lane c, $4.3\times10^6$ dpm in lane d, and $2.1\times10^6$ dpm in lanes f and g. Hind III fragments of lambda DNA (3,000 dpm in 0.6 ug) were used as standards for size determination in lane e.

Comparison of the pattern of repeated Bam HI fragments in lane d (R500 DNA) and lane a (NIH 3T3 DNA) reveals a large number of amplified fragments in the R500 DNA which are not present in NIH 3T3 DNA (indicated by arrowheads). These fragments are readily detectable in lane c (50 copies of the DHFR gene) but not in lane b (20 copies of the DHFR gene). Assuming that the degree of amplification of these fragments corresponds to that of the DHFR gene, the sensitivity of the method is between 20 and 50 copies of an amplified DNA fragment per haploid mammalian genome This estimate is in good agreement with the results of other experiments where gene amplification was simulated by the addition of varying amounts of λ phage DNA to mammalian DNA prior to restriction enzyme digestion. It was found that λ DNA fragments were detectable when added in the amount corresponding to 30 copies of λ DNA per haploid mammalian genome, but not at 15 copies per genome. The similarity of the estimated limits of sensitivity for the completely homogeneous λ DNA fragments (between 15 and 30 copies per genome) and for the fragments of the amplified DNA in MTX-resistant cells (between 20 and 50 copies) indicates that different individual units of amplified DNA, that arose relatively recently, in the course of selection for MTX-resistance, have not accumulated a significant amount of base sequence divergence and therefore have a high efficiency of ingel renaturation. This property distinguishes the amplified DNA fragments from repeated DNA fragments, which have accumulated a high degree of base sequence divergence in the course of evolution, and were found to reanneal in the gel at a much lower efficiency than λ DNA fragments, as was estimated by the intensity of the corresponding bands. It should also be noted that detection is higher for the genomes of a smaller size. Thus, when λ DNA was combined with chicken DNA, it was possible to detect λ DNA fragments at mere 15 copies per haploid chicken genome.

The amplified DNA fragments in R.3 cells, which contain only 16 copies of the DHFR gene, were not detectable in lane f, where R.3 DNA was used both as a tracer and as a driver. However, the use of R.3 DNA as a tracer in combination with R500 DNA (170 copies of the DHFR gene) as a driver, permitted identification of several amplified fragments (indicated with arrowheads in lane g). These fragments have been commonly amplified in two independently derived MTX-resistant lines, R500 and R.3 and therefore are likely to contain the DHFR gene itself. The procedure thus allows both detection of amplified DNA sequences in the absence of any cloned probes and identification of a subset of commonly amplified sequences which are likely to contain the amplified gene, which served as a target for selection and is responsible for the particular cell phenotype. Once identified, these DNA sequences can be subsequently cloned and analyzed, as illustrated below.

EXAMPLE IV

Cloning of an amplified DNA fragment.

Mammalian cells selected for resistance to certain cytotoxic drugs frequently develop cross-resistance to a broad spectrum of other drugs unrelated in structure to the original selective agent. This phenomenon of multidrug resistance constitutes a major problem in cancer chemotherapy. DNA from several independently derived multidrug resistant cell lines was assayed for the presence of amplified DNA sequences by in-gel renaturation, using the approach that was described in Example III. Two multidrug resistant Chinese hamster cell lines, one of which was selected for resistance to Adriamycin and the other for resistance to colchicine were found to contain amplified DNA fragments. Among the amplified fragments generated by digestion with Bam HI, nine were found to be amplified in common in these two lines. In order to analyze the function of these commonly amplified DNA sequences, it was important to clone at least one of the restriction fragments. The 1.1 kb amplified Bam HI fragment was purified and cloned in the following mode.

DNA from a cell line, LZ, which was selected for resistance to Adriamycin, was digested with Bam HI. 100 μg of the digest were electrophoresed in a 1% agarose gel. Position of the 1.1 kb fragment was identified in the gel, and the corresponding strip of agarose was cut out. The gel was subjected to two cycles of denaturation and renaturation without S1 nuclease digestion, as described. DNA was eluted from the gel and ligated to the plasmid pBR322 which had been previously cleaved with Bam HI to yield recombinant DNA plasmids. The plasmids were used to transform *Escherichia coli* HB101 and plasmid DNA from the resulting ampicillin-resistant/tetracyclinesensitive colonies was analyzed by mini-scale DNA extraction and digestion with Bam HI and HinfI. Of 35 samples of the recombinant plasmids, seven produced identical restriction patterns, indicating that the corresponding clones contained DNA inserts that were reiterated in the genome. DNA from one of these clones, designated pDR1.1, was used for hybridization with Bam HI-digested genomic DNA. The results of hybridization are illustrated in FIG. 4.

Figure 4:
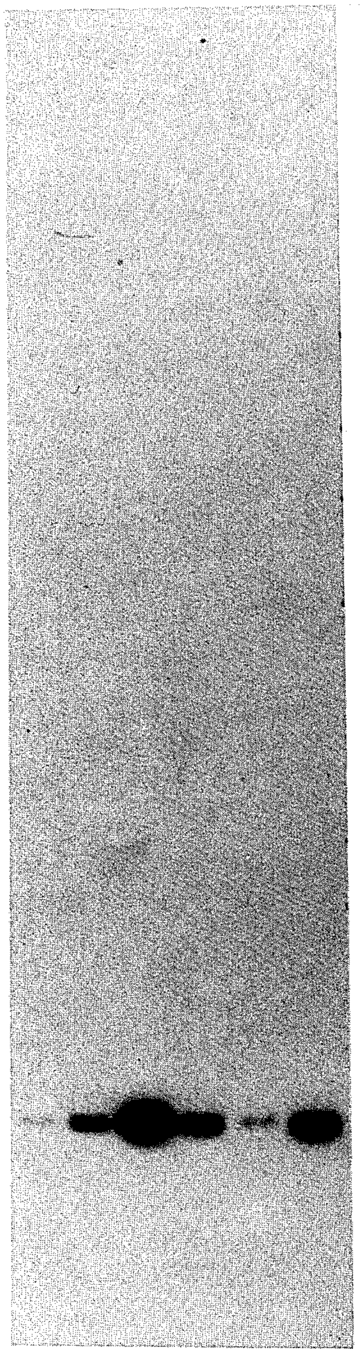
FIG. 4 is an autoradiogram illustrating amplification of a cloned restriction fragment in multidrug-resistant Chinese hamster cell lines.
Figure 4:
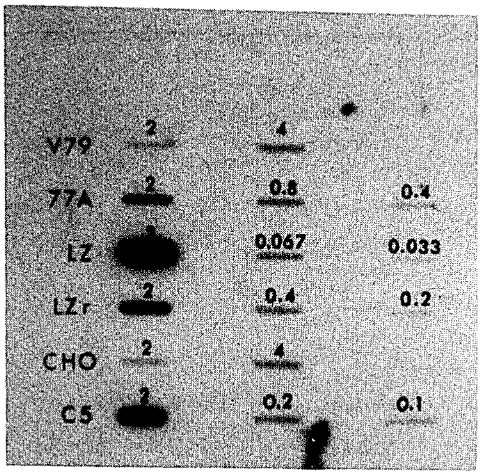

The autoradiograms represented in FIG. 4 contained the following:

Autoradiogram a represents the Southern blot hybridization of pDR1.1, labeled by nick-translation [Rigby et al., *J. Mol. Biol.* 113:237–251 (1977)]with Bam HI-digested genomic DNA, electrophoresed in a 1% agarose gel and transferred to a nitrocellulose filter.

Lane 1 contains DNA from a drug-sensitive cell line V79. Lane 2 contains DNA from a cell line 77A, derived from V79 and selected for resistance to a 5-fold relative concentration of Adriamycin. Lane 3 contains DNA from a cell line LZ, derived from 77A and selected for resistance to a 3,000-fold relative concentration of Adriamycin. Lane 4 contains DNA from LZ cells that were grown in the absence of the drug for a period of 130 cumulative doublings and have reverted to a lower degree of resistance, corresponding to a 7-fold relative concentration of Adriamycin. Lane 5 contains DNA from a drug-sensitive cell line CHO Aux B1. Lane 6 contains DNA from a cell line C5, derived from CHO Aux B1 and selected for resistance to a 280-fold relative concentration of colchicine and cross-resistant to a 150-fold relative concentration of Adriamycin. Each lane contains 5 μg of genomic DNA. The filter was hybridized with $3\times10^7$ dpm of pDR1.1 plasmid DNA (specific activity $2\times10^8$ dpm/μg).

Autoradiogram b represents the slot-blot hybridization [Brown et al., *Mol. Cell. Biol.* 3:1097–1107 (1983)] of pDR1.1 with genomic DNA. The source and amount (in μg) of DNA in each slot are indicated. The blot was hybridized with $3\times10^7$ dpm of the pDR1.1 probe.

The results of the assays shown in FIG. 4 indicate that the 1.1 kb Bam HI fragment is amplified in all drug-resistant lines relative to the parental drug-sensitive lines. The degree of amplification was estimated as 5-fold in 77A DNA, 60-fold in LZ DNA, 10-fold in LZ revertant DNA and 20-fold in C5 DNA. The correlation between the degree of amplification of the cloned DNA sequences and the degree of drug-resistance indicated that the amplified DNA sequences are likely to be responsible for multidrug resistance in mammalian cells.

The procedure for detection and cloning of amplified DNA, as illustrated in Examples III and IV, is generally applicable for isolation of any amplified gene of interest or any repeated DNA fragment. This application of the present invention should be of particular importance in the field of cancer therapy, where gene amplification may be involved in the development of tumor resistance to different types of therapy. Isolation of amplified genes involved in the resistance phenotype may lead to development of new approaches to cancer diagnosis and treatment.

It will be appreciated that these applications of the method described herein are obvious extensions and uses of the basic methodology. The invention, therefore, is not to be restricted in form or limited in scope except by the claims appended hereto.

I claim:

1. A method for detecting and isolating individual nucleic acid sequences commonly held by a plurality of different double stranded nucleic acids of interest comprising the steps of:

- obtaining a plurality of different double stranded nucleic acids of interest;
- converting said double stranded nucleic acids into a plurality of double stranded nucleic acid fragments with an endonuclease composition containing at least one endonuclease, said endonuclease composition being the same for each sample of nucleic acid of interest;
- introducing an identifiable label into one of the nucleic acids of interest;
- combining said labelled nucleic acid with at least one other unlabelled nucleic acid of interest to form a mixture;
- subjecting said mixture of double-stranded nucleic acid fragments to gel electrophoresis whereby a plurality of separated, double-stranded nucleic acid molecules are individually localized in the gel;
- denaturing in said gel said separated nucleic acid molecules to form single-stranded molecules;
- renaturing in said gel at least a portion of said single-stranded nucleic acid molecules to form reannealed doublestranded molecules;
- eliminating such single-stranded nucleic acid molecules as remains in said gel; and
- detecting said identifiable label within said reannealed double-stranded nucleic acid molecules whereby the individual nucleic acid sequences commonly held are isolated.

2. A method for detecting and isolating individual nucleic acid sequences repeated seriatim within a doublestranded nucleic acid of interest comprising the steps of:

- obtaining a double stranded nucleic acid of interest;
- converting said double-stranded nucleic acids into a plurality of double-stranded nucleic acid fragments with an endonuclease composition containing at least one endonuclease,
- introducing an identifiable label into at least a portion of said nucleic acid fragments said portion having the same composition of different nucleic acid fragments as the nucleic acid fragments obtained from said converting step;
- combining said labelled nucleic acid fragments of interest with unlabelled nucleic acid fragments of interest to form a mixture;
- subjecting said double-stranded nucleic acid fragments to gel electrophoresis whereby a plurality of separated, double-stranded nucleic acid molecules are individually localized in the gel;
- denaturing in said gel said separated nucleic acid molecules to form single-stranded nucleic acid molecules;
- renaturing in said gel at least a portion of said single-stranded nucleic acid molecules to form reannealed doublestranded molecules;
- eliminating such single-stranded nucleic acid molecules as remains in said gel; and
- detecting said identifiable label within said reannealed double-stranded nucleic acid molecules whereby the individual nucleic acid sequence repeated seriatum are isolated.

3. The method as recited in claim 12 or 13 further comprising:

- excising that portion of said gel containing individually localized, double-stranded nucleic acid molecules;
- denaturing said separated nucleic acids within said excised portion of said gel into single-stranded molecules;
- renaturing in said excised gel at least a portion of said single-stranded nucleic acid molecules into double-stranded molecules; and
- disrupting such single-stranded nucleic acid molecules as remains in said excised gel.

4. The method as recited in claim 12 or 13 further comprising:

- excising that portion of said gel containing an individually localized, separated, double-stranded nucleic acid molecules;

denaturing the nucleic acids within said excised portion of said gel into single-stranded nucleic acid molecules;

renaturing at least a portion of said single-stranded nucleic acid molecules into double-stranded nucleic acid molecules; and eliminating such single-stranded nucleic acid molecules as remains in said excised gel by selectively cloning said reannealed double-stranded nucleic acid molecules.

5. The method of claim 1 or 2 which includes the additional steps of:

purifying said reannealed double-stranded molecules by excising the portion of said gel containing such reannealed molecules and eluting such reannealed molecules from said gel;

cloning said purified molecules as recombinant DNA clones; and testing individual recombinant DNA clones for the presence of the isolated nucleic acid sequences of interest.

6. The method as recited in claim 1 or 2 wherein the nucleic acid sequences comprise deoxyribonucleic acids.

7. The method as recited in claim 1 or 2 wherein the nucleic acid sequences comprise ribonucleic acids.

8. The method as recited in claim 1 or 2 wherein said identifiable label is a radionuclide.

9. The method as recited in claim 1 or 2 wherein said nucleic acid molecules are denatured prior to separation.

10. The method as recited in claim 1 or 2 wherein said eliminating step comprises combining said reannealed double-stranded molecules with a nuclease specific for single-stranded nucleic acid sequences.

11. The method as recited in claim 1 or 2 wherein said steps of denaturation, renaturation and elimination of single-stranded nucleic acid sequences are repeated prior to said detection of the identifiable label within said reannealed double-stranded molecules.

* * * * *